(12) United States Patent
Yassour et al.

(10) Patent No.: US 6,673,089 B1
(45) Date of Patent: *Jan. 6, 2004

(54) IMPLANTABLE STROKE TREATING DEVICE

(75) Inventors: Yuval Yassour, Haifa (IL); Ofer Yodfat, Reut (IL); Ygael Grad, Tel Aviv (IL); Moshe Rosenfeld, Beit Halevy (IL); Daniel Levin, Haifa (IL)

(73) Assignee: Mindguard Ltd., Caesarea (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/637,287

(22) Filed: Aug. 11, 2000

Related U.S. Application Data

(63) Continuation-in-part of application No. 09/484,965, filed on Jan. 18, 2000.

(30) Foreign Application Priority Data

Mar. 11, 1999 (IL) .................................................. 128938

(51) Int. Cl.⁷ ............................................... A61M 29/00
(52) U.S. Cl. ...................................... 606/200; 623/1.39
(58) Field of Search ........................... 606/1, 108, 198, 606/200; 623/1.1, 1.11, 1.12, 1.13, 1.39, 1.4

(56) References Cited

U.S. PATENT DOCUMENTS

| | | | |
|---|---|---|---|
| 5,807,330 A | 9/1998 | Teitelbaum | |
| 5,876,367 A | 3/1999 | Kaganov et al. | |
| 5,941,986 A | 8/1999 | Kerr | |
| 5,951,599 A | 9/1999 | McCrory | |
| 6,146,370 A | 11/2000 | Barbut | |
| 6,258,115 B1 * | 7/2001 | Dubrul | 606/200 |
| 6,258,120 B1 | 7/2001 | McKenzie et al. | |
| 6,261,305 B1 * | 7/2001 | Marotta et al. | 606/200 |
| 6,348,083 B1 * | 2/2002 | Yassour et al. | 606/200 |

FOREIGN PATENT DOCUMENTS

| | | |
|---|---|---|
| EP | 0 880 948 A1 | 12/1988 |
| WO | WO 98/47447 | 10/1998 |
| WO | WO 98/58599 | 12/1998 |
| WO | WO 99/32050 | 7/1999 |

\* cited by examiner

*Primary Examiner*—Aaron J. Lewis
(74) *Attorney, Agent, or Firm*—G. E. Ehrlich Ltd.

(57) ABSTRACT

An implantable device for positioning in the vicinity of the bifurcation of the common carotid artery (CCA) into the internal carotid artery (ICA) and the external carotid artery (ECA) comprises a deflecting element suitable to deflect the flow of embolic material flowing in the CCA toward the ICA, into the ECA.

24 Claims, 7 Drawing Sheets

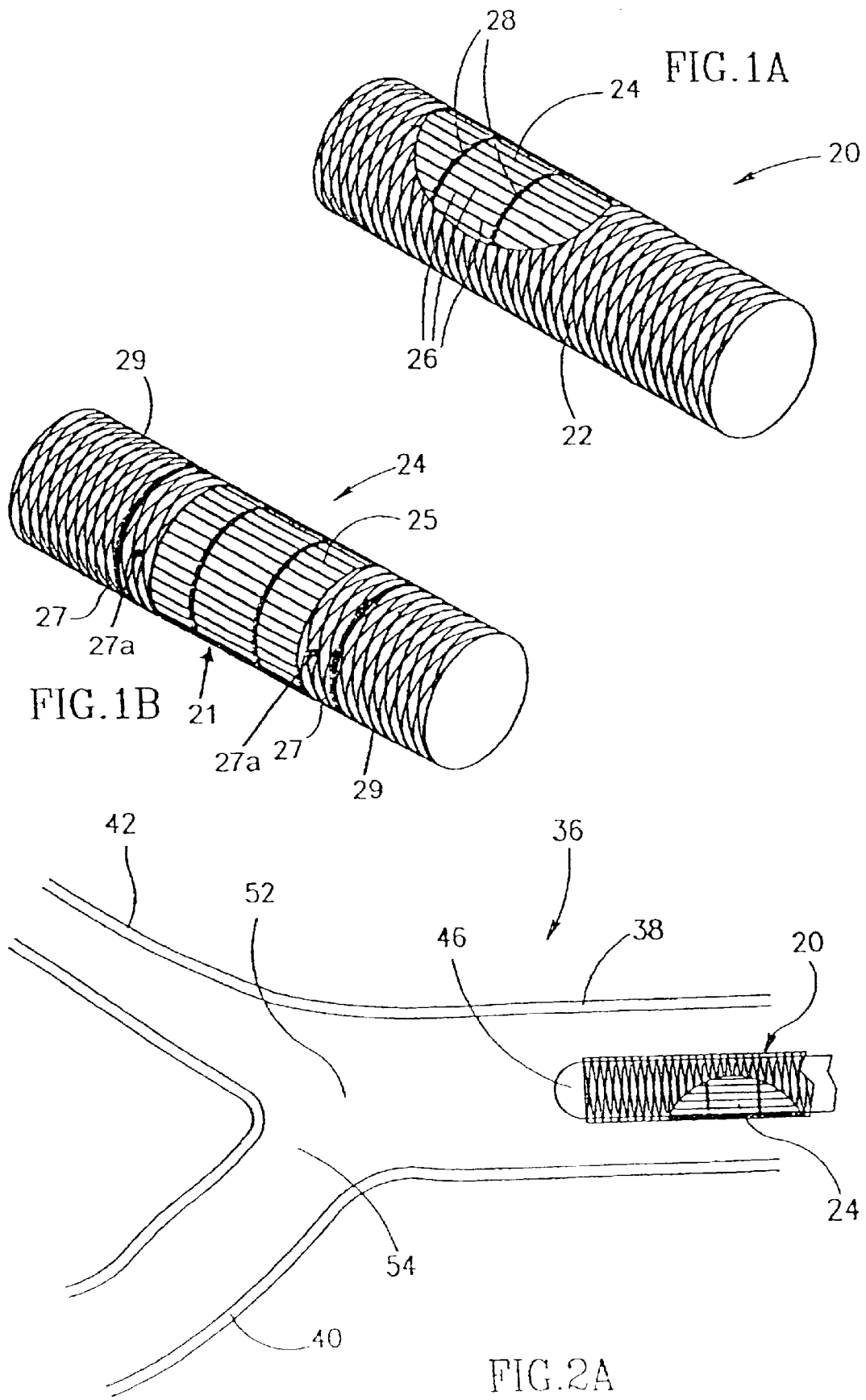

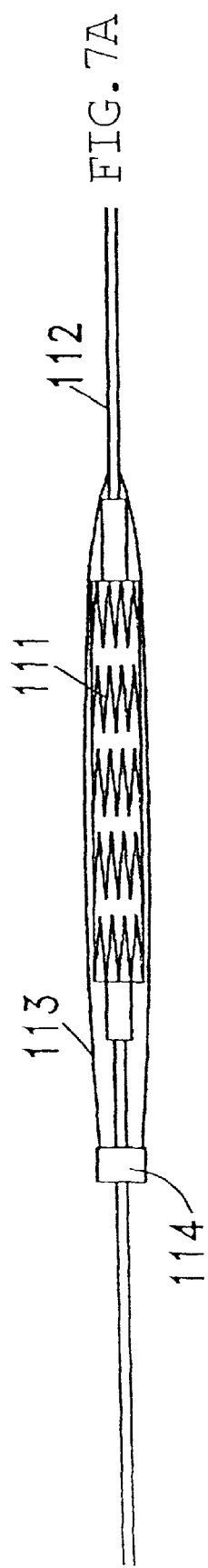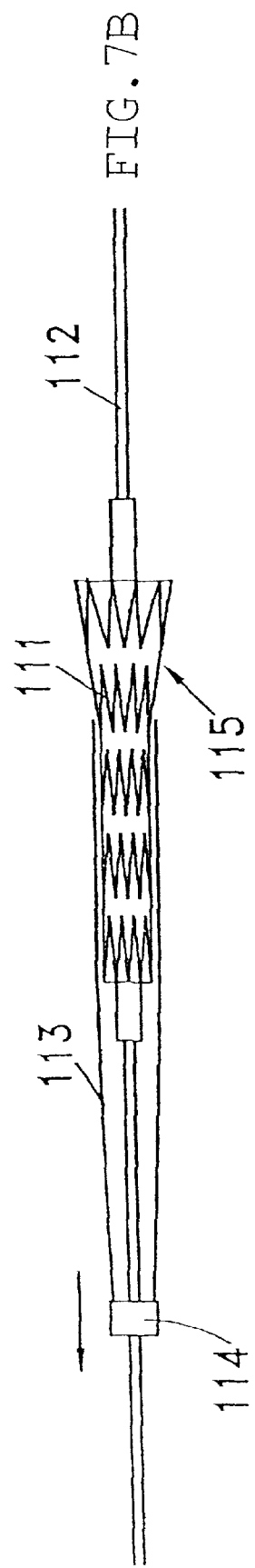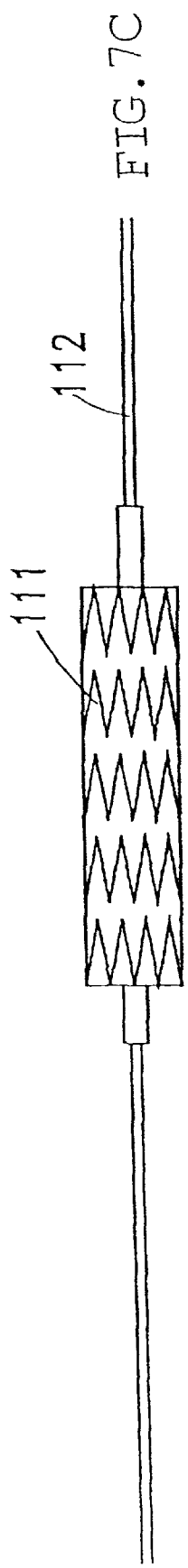

IMPLANTABLE STROKE TREATING DEVICE

This is a Continuation-in-Part of copending application Ser. No. 09/484,965, filed Jan. 18, 2000.

FIELD OF THE INVENTION

The present invention relates to implantable stroke treating devices, and more specifically is concerned with a device for reducing the risk of embolic material entering into the internal carotid artery of an individual and blood clots (collectively and interchangeably referred to as "embolic material").

BACKGROUND OF THE INVENTION

A major portion of blood supply to the brain hemispheres is by two arteries, referred to as common carotid arteries (CCA), each of which branches off, or bifurcates as the term is at times used, into a so-called internal carotid artery (ICA) and an external carotid artery (ECA). Blood to the brain stem is supplied by two vertebral arteries.

Cerebralvascular diseases are considered among the leading causes of mortality and morbidity in the modern age. Strokes denote an abrupt impairment of brain function caused by pathologic changes occurring in blood vessels. The main cause of strokes is insufficient blood flow to the brain (referred to as "an ischemic stroke") which are about 80% of stroke cases.

Ischemic strokes are caused by sudden occlusion of an artery supplying blood to the brain. Occlusion or partial occlusion (stenosis) are the result of diseases of the arterial wall. Arterial atherosclerosis is by far the most common arterial disorder, and when complicated by thrombosis or embolism it is the most frequent cause of cerebral ischemia and infarction, eventually causing the cerebral stroke.

Cardioembolism causes about 15%–20% of all strokes. Stroke caused by heart disease is primarily due to embolism of thrombotic material forming on the atrial or ventricular wall or the left heart valves. These thrombi then detach and embolize into the arterial circulation. Emboli large enough can occlude large arteries in the brain territory and cause strokes.

Cardiogenetic cerebral embolism is presumed to have occurred when cardiac arrhythmia or structural abnormalities are found or known to be present. The most common causes of cardioembolic stroke are nonrheumatic (nonvalvular) atrial fibrillation (AE), prothestic valves, rheumatic heart disease (RHD), ischemic cardiomyopathy, congestive heart failure, myocardial infarction, post-operatory state and protruding aortic arch atheroma (A.A.A.).

Such disorders are currently treated in different ways such as by drug management, surgery (carotid endarterectomy) in case of occlusive disease, or carotid angioplasty and carotid stents.

While endarterectomy, angioplasty and carotid stenting are procedures targeting at opening the occluded artery, they do not prevent progression of new plaque. Even more so, the above treatment methods only provide a solution to localized problems and do not prevent proximal embolic sources, i.e. embolus formed at remote sites (heart and ascending aorta) to pass through the reopened stenosis in the carotid and occlude smaller arteries in the brain. This is a substantial problem, inasmuch as about one-third of patients suffering from carotid occlusion also have proximal embolic sources leading to stroke. It should be noted that only about 20% of the cases of stroke result from an occlusion of the carotid.

It will also be appreciated that endarterectomy is not suitable for intracarnial arteries or in the vertebrobasilar system since these arteries are positioned within unacceptable environment (brain tissue, bone tissue) or are too small in diameter.

Introducing filtering means into blood vessels, in particular into veins, has been known for some time. However, filtering devices known in the art are generally of a complex design, which renders such devices unsuitable for implantation within carotid arteries, and unsuitable for handling fine embolic material. However, when considering the possible cerebral effects of even fine embolic material occluding an artery supplying blood to the brain, the consequences may be fatal or may cause irreversible brain damage.

However, in light of the short period of time during which brain tissue can survive without blood supply, there is significant importance to providing suitable means for preventing even small embolic material from entering the internal carotid artery, so as to avoid brain damage.

A drawback of prior art filtering means is their tendency to become clogged. On the one hand, in order to provide efficient filtering means, the filter should be of fine mesh. On the other hand, a fine mesh has a higher tendency toward, and risk of, occlusion.

It should also be noted that the flow ratio between the ICA and the ECA is about 4:1. This ratio also reflects the much higher risk of embolic material flowing into the ICA.

It is thus an object of the present invention to provide an implantable deflecting device suitable to be positioned within a blood vessel supplying blood to the brain, and further suitable to deflect embolic material that would have flown into the internal carotid artery, into the external carotid artery, thereby preventing the entry of said embolic material into the internal carotid artery, and thus preventing extra-carnial embolus to occlude small intercarnial arteries in the brain.

It is another object of the invention to provide a method for treating a patient known to suffer from embolic diseases, by selectively occluding the passage of embolic material into the internal carotid artery.

It is yet another object of the invention to provide a method for preventing conditions associated with embolic material.

Other objects of the invention will become apparent as the description proceeds.

SUMMARY OF THE INVENTION

The present invention provides an implantable device for positioning in the vicinity of the bifurcation of the common carotid artery (CCA) into the internal carotid artery (ICA) and the external carotid artery (ECA), comprising a deflecting element suitable to deflect the flow of embolic material flowing in the CCA toward the ICA, into the ECA. Preferably, but non-limitatively, the deflecting element comprises filtering means.

Thus, in one aspect, the invention provides an implantable deflecting device comprising an anchoring member engageable with inner walls of a carotid artery, and one or more deflecting members for deflecting flow of embolic material into the ECA, substantially without obstructing blood flow into the ICA.

The anchoring member and the deflecting member may be integral with one another or attached or coupled to one another. In the present specification the anchoring member and the deflecting member may be referred to also as anchoring portion and deflecting portion, respectively.

In accordance with a particular preferred embodiment of the invention, the deflecting member is a screening element fitted at the inlet into the ICA and is adapted to prevent the passage into the ICA of embolic material above a predetermined size.

By a preferred embodiment, at least the anchoring member is a stent adapted for insertion via the vasculature of an individual. The implantable deflecting device in accordance with any of the embodiments of the present invention may be permanently implanted or may be removed after a period of time, depending on the course of treatment and the medical procedure.

As will become evident from the description to follow, the deflecting member is preferably, but not compulsorily, positioned at the inlet into the internal carotid artery, whereas the anchoring member may be positioned in a variety of locations. The deflecting member, however, may be positioned at any location that fulfills two conditions: firstly, it does not occlude the flow of blood into the ICA, and secondly, it causes a deflection of the flow of embolic material into the ECA. For instance, the deflecting member may be anchored in the ICA and protrude into the bifurcation zone, or may be positioned at the entrance to the ECA and extend toward the surrounding walls, for constructive and strength reasons.

In accordance with one specific embodiment of the invention, the anchoring member comprises a tubular portion for anchorage within the CCA with an upstream portion extending towards the bifurcation zone, said upstream portion accommodating the one or more deflecting member.

In accordance with still another preferred embodiment of the invention, the anchoring member comprises a tubular portion for anchoring within the ECA, with a downstream portion extending towards the bifurcation zone, said downstream portion accommodating the one or more deflecting member. Alternatively, the anchoring member comprises a tubular portion for anchorage within the ICA, with a downstream portion extending towards the bifurcation zone, said upstream portion accommodating the one or more deflecting member.

It will also be appreciated that the anchoring member may comprise a tubular portion for anchorage within a vascular portion extending along the CCA and the ECA, wherein the one or more deflecting members is accommodated at the inlet to the ICA.

By one specific design the anchoring member comprises a tubular portion for anchorage at the bifurcation zone, wherein the one or more deflecting member is accommodated at or adjacent the inlet into the ICA.

The one or more deflecting member may be integrally formed with the anchoring member or may be attached or coupled thereto either during manufacture, or after implanting the anchoring member within the artery.

By another aspect of the present invention there is provided an implantable deflecting device for implanting at the vicinity of bifurcation of the common carotid artery (CCA) into the internal carotid artery (ICA) and the external carotid artery (ECA); the device comprising an anchoring member engageable with inner walls of a carotid artery, and one or more deflecting members, wherein the one or more deflecting member is so positioned and sized so that embolic material encountering it is deflected to flow into the ECA.

In another aspect the invention is directed to an arterial stent suitable to be positioned in the vicinity of the bifurcation of the common carotid artery (CCA) into the internal carotid artery (ICA) and the external carotid artery (ECA), comprising a deflecting device.

The invention is further directed to an arterial stent suitable to be positioned in the vicinity of the bifurcation of the common carotid artery (CCA) into the internal carotid artery (ICA) and the external carotid artery (ECA), coupled to a deflecting device.

Preferably, but non-limitatively, the aforementioned stents employ as a deflecting device an element comprising filtering means of dimensions suitable to allow the flow of blood to proceed into the ICA, while preventing the access thereto of embolic material of a predetermined size.

In a further aspect, the invention is directed to the prevention of the occurrence, or the recurrence, of cerebralvascular diseases, particularly of stroke, comprising preventing the flow of embolic material flowing in the CCA from accessing the ICA, by deflecting the flow of said embolic material into the ECA. Prevention of the cerebralvascular disease is achieved by implanting, permanently or temporarily, in the vicinity of the bifurcation of the common carotid artery (CCA) into the internal carotid artery (ICA) and the external carotid artery (ECA), a deflecting device according to the invention.

It should be emphasized that while throughout this specification reference is made to the bifurcation of the CCA into the ICA, this is done for the sake of brevity only, but the invention is in no way limited to this specific location. The invention can be advantageously be exploited at any other suitable bifurcation of blood vessels as existing, for instance, in the leg.

All the above and other characteristics and advantages of the invention will be better understood through the following illustrative and non-limitative detailed description of preferred embodiments thereof.

BRIEF DESCRIPTION OF THE DRAWINGS

In order to better understand the invention and to illustrate it in practice, non-limiting examples of some preferred embodiments will now be described, with reference to the accompanying drawings, in which:

FIG. 1A is a perspective view of a deflecting member in accordance with a preferred embodiment of the present invention;

FIG. 1B is a perspective view of a deflecting member according to another preferred embodiment of the invention, which is a modification of the device of FIG. 1A;

FIG. 2 illustrates the insertion and positioning of a device according to a preferred embodiment of the invention:

FIG. 2A schematically shows the deflecting device of FIG. 1, in collapsed form (i.e., prior to expansion into the artery), on its way to reach the arterial bifurcation.

FIGS. 7A, 7B, and 7C schematically illustrate the insertion of a self-expandable device; and;

DETAILED DESCRIPTION OF PREFERRED EMBODIMENTS

Figure 2B:
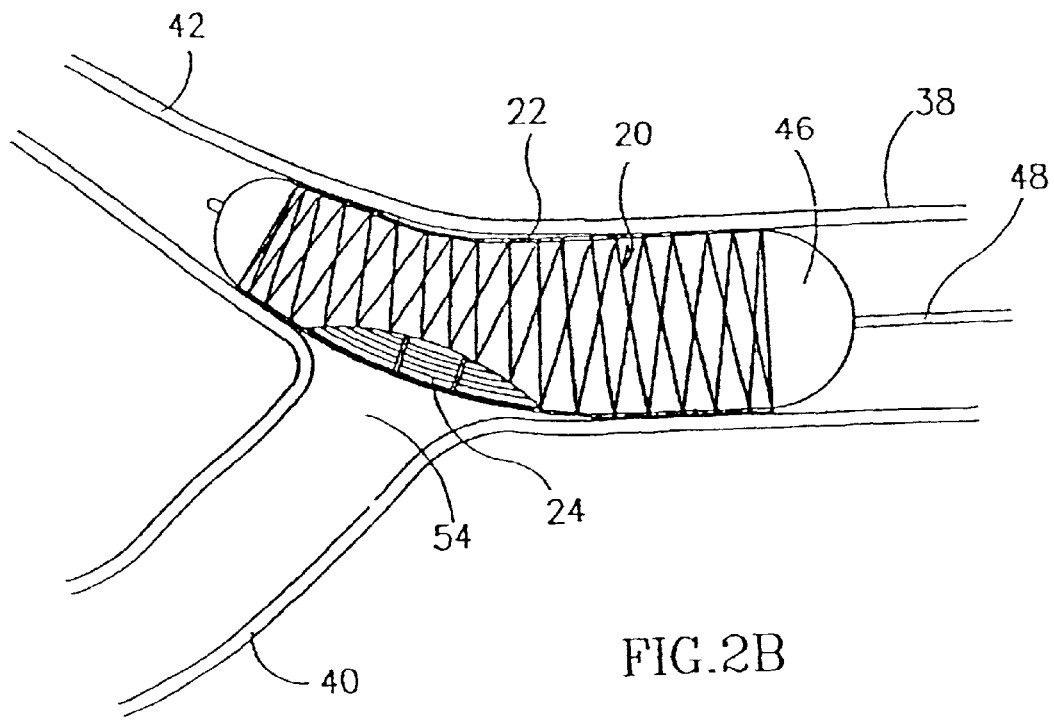
FIG. 2B schematically shows the deflecting device of FIG. 2A, during its expansion and positioning at the arterial bifurcation.

A deflecting device in accordance with a preferred embodiment of the present invention, generally designated 20, is shown in FIG. 1A. The deflecting device is made of fine wire woven into a net-like device having a construction suitable for expanding from a contracted position in which it is deployed through the vasculator of an individual and expanded by means well known in the art, as will be further explained hereinafter with reference to FIGS. 2A and 2B.

The deflecting device 20 has an essentially cylindrical shape with its body 22 generally serving as an anchoring portion. An anchoring portion is a portion of the device that firmly contacts the walls of the artery. Such contact causes a growth of the wall into the net of the devices, and strongly anchors it to the artery thus preventing its accidental displacement. The physiological processes leading to such anchoring are well known in the art, and will therefore not be discussed herein in detail, for the sake of brevity.

A deflecting portion 24 is constructed by a plurality of fine wires 26, parallely extending along the longitudinal axis of the device and supported by two support wires 28. The deflecting portion 24 is integral with or attached to the anchoring portion 22.

The size and shape of the deflecting member is adjusted to match the inlet of the internal carotid artery as will be further explained hereinafter.

The embodiment of FIG. 1B is similar to that of FIG. 1A. However, the deflecting device 21, which is essentially cylindrical, comprises a deflecting portion 25 which is not limited to a part of the circumference of the device, as is the deflecting portion 24 of FIG. 1A, but rather covers the whole circumference of the device. This arrangement, of course, is easier to use, in as much as there is no need to exactly match the limited area of the deflecting portion with the opening of the ICA. Furthermore, two markers 27 (which in the particular embodiment of FIG. 1B are circular in shape) are provided, which are radio opaque and serve to aid a physician in the proper positioning of the device within the artery. The markers are visible under radiographic equipment, and therefore can be used to follow the advancement of the device that bears them. Other markers can also be provided, as will be apparent to the skilled person. For instance, markers 27a are gold points which may be used to position the device also with respect of its rotation around its axis.

The structure of the anchoring portion 29 and of the deflecting portion 25 is essentially similar to the structure illustrated with reference to FIG. 1A. The difference resides mainly in the design of the deflecting portion, and in the provision of the markers.

Figure 2C:
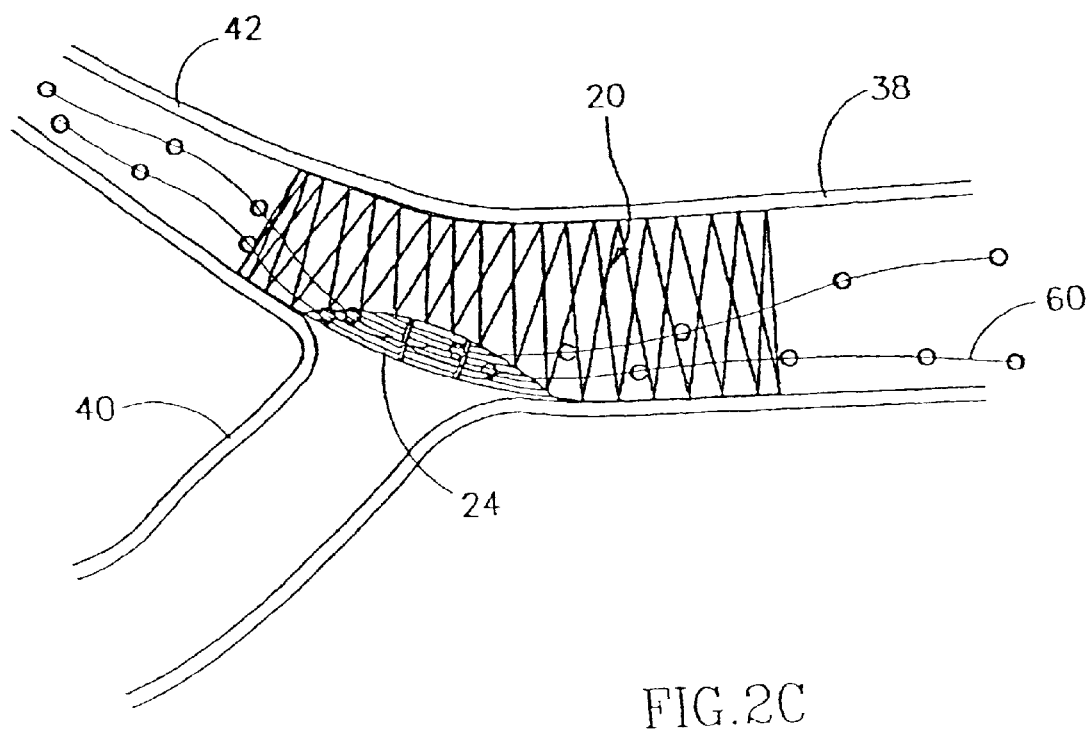
FIG. 2C shows a situation in which the device of FIG. 1 has been positioned in the bifurcation, and the deploying equipment has been withdrawn (normal working position)

FIGS. 2A through 2C illustrates a carotid artery portion, generally designated 36, in which the common carotid artery (CCA) is designated 38, the internal carotid artery (ICA) is designated 40, and the external carotid artery (ECA) is designated 42. For placing the deflecting device 20 seen in FIG. 1, conventional stent deployment equipment may be used, which equipment typically comprises an expandable balloon 46, fitted at an end of an inflating tube 48 carried by a guide wire (not seen). However, the device may also be self-expandable, as known per se, and as readily understood by the skilled person.

The arrangement is such that by using suitable imaging equipment, the assembly seen in FIG. 2A is inserted through the vasculator of an individual, into the CCA, until the deflecting device 20 is positioned within the bifurcation zone 52, with the deflecting member 24 extending opposite inlet 54 of ICA 40. In this position, balloon 46 is inflated, as shown in FIG. 2B, whereby the anchoring walls 22 of deflecting device 20 anchor against respective inner walls of the common carotid artery 38 and the external carotid artery 42, respectively, with the deflecting member 24 extending across inlet 54 of the internal carotid artery 40. Then, balloon 46 is deflated and is removed via the vasculator of the individual, and the deployment of the deflecting member 20 is thus completed, as seen in FIG. 2C. In this position, embolic material, which is schematically illustrated as particles flowing along flow lines 60 in FIG. 2C, flow in the common carotid artery 38, and upon meeting the deflecting member 24 they are prevented from entering the ICA 40, because their size is larger than the mesh of deflecting portion 24, and they are thus deflected into the external carotid artery 42.

The corresponding operation, when effected with a self-expandable stent, is illustrated in FIG. 7. As will be apparent to the skilled person, using a self-expandable device is more convenient in many cases, because of the great mobility of the neck of the patient. The self-expandable device, of course, provides for a better anchoring of the device.

FIG. 7A shows the stent in folded state, FIG. 7B shows it during the first stage of expansion, and FIG. 7C shows it in fully expanded state. The stent 111 is supported on a guide wire 112, which is used to introduce and guide it to the desired location. In its folded position, stent 111 is covered with a covering envelope 113, which may be made of polymeric material, which keeps it in its folded state. Envelope 113 is connected to a retraction ring 114, which can be pulled away from stent 111 by means not shown in the figure and well known to the skilled person. Looking now at FIG. 7B, when ring 114 is pulled away in the direction of the arrow, envelope 113 is pulled away with it, uncovering a portion of the stent, indicated at 115. Since the envelope no longer obliges this portion 115 to remain in the folded position, and since the normal position of the stent is expanded, this portion starts expanding to its natural, expanded state. This process is completed in FIG. 7C, when the envelope has been completely removed and the stent is in its fully expanded position. Because elastic forces operate to keep the stent expanded, its anchoring in its location is less susceptible of undesired displacement than balloon expanded stents. Of course, the guide wire is withdrawn from the patient after the positioning of the stent and its expansion is completed, as in any other similar procedure.

Figure 3A:
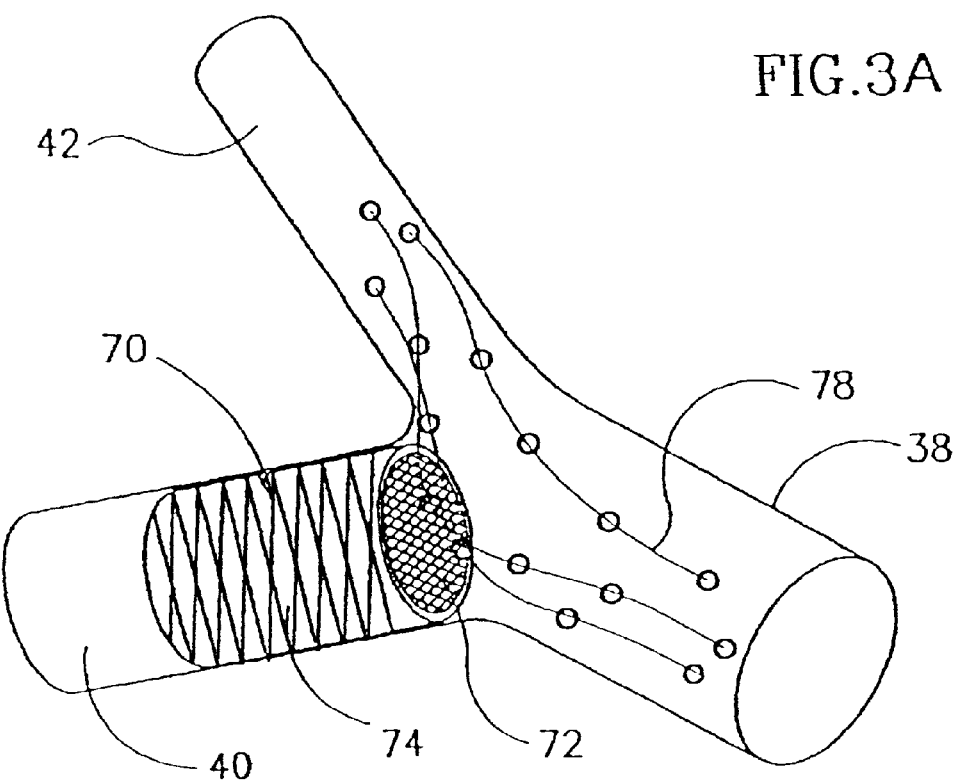
FIG. 3A schematically illustrates a deflecting device in accordance with another embodiment of the invention, located within the internal carotid artery.

Looking now at FIG. 3A, a further preferred embodiment of the invention is illustrated, in which the same reference numerals are used to denote the artery parts. In this preferred embodiment of the invention, the deflecting device, generally indicated by numeral 70, is anchored within the internal carotid artery 40 with the deflecting member 72 extending downstream at the base of the substantially cylindrical deflecting member 70.

Figure 3D:
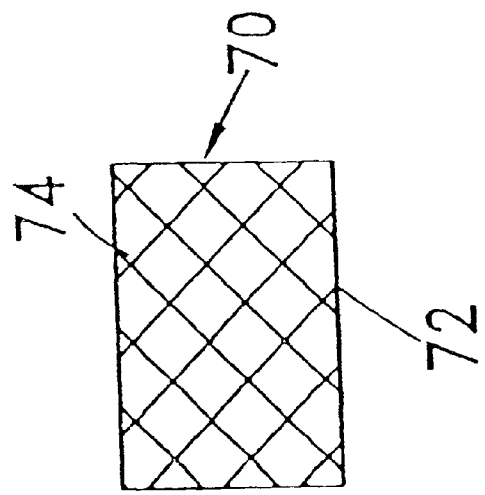
FIGS. 3B, 3C, and 3D schematically illustrate the stages of insertion of the device of FIG. 3A.
Figure 3C:
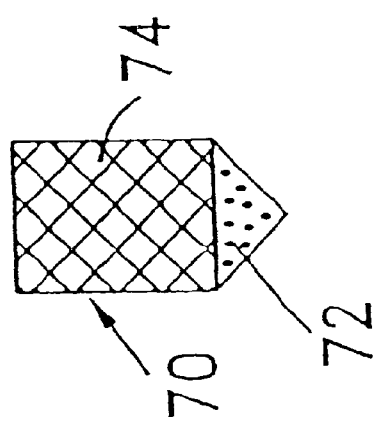
Figure 3B:
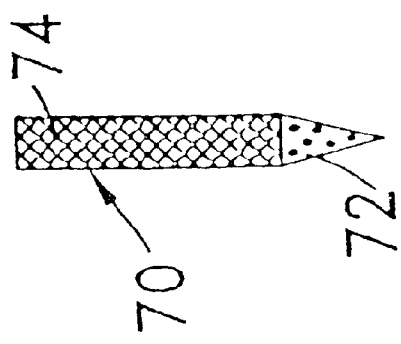

In accordance with this embodiment of the invention it is possible that the deflecting device 70 comprises a separate anchoring member 74 which is first deployed and anchored within the ICA 40 and then only the deflecting member 72 is attached thereto. According to a preferred embodiment of the invention, however, deflecting device 70 is inserted as schematically illustrated in FIGS. 3B–3D. In the first stage (FIG. 3B), the device is folded so that the anchoring member 74 has a diameter of about 3 mm. The deflecting member 72 is protruding outside the tubular body of anchoring member 74. FIG. 3C shows the second stage, in which partial expansion of anchoring body 74 has taken place, which leads to a partial retraction of deflecting member 72. Finally (FIG. 3D), in the third stage the anchoring member 74 is fully expanded, to a diameter of about 7–9 mm, and deflecting member 72 has withdrawn to a plane substantially perpendicular to the axis of tubular anchoring member 74. According to this particular embodiment of the invention, deflecting member 72 has a net-like configuration.

Lines 78 schematically represent the flow of embolic material entering from the common carotid artery 38 and deflected into the ECA 42, rather than entering the ICA 40. Since the deflecting portion 72 is made of mesh material, on the other hand, blood is free to flow into the ICA 40. As will be appreciated by the skilled person, it is required that the mesh deflecting element be of a mesh size sufficient to allow passage of blood without hindrance, while occluding the passage of embolic material of predetermined size. Typically—but non-limitatively—the deflecting member is designed so as to prevent the passage of particles of a size in the range of 200–400 $\mu$m. This is a substantial improvement over the prior art that aims at excluding particles of about 1 cm diameter. This is made possible, according to the invention, by the fact that the device employed is a deflecting device, and thus clogging problems that are present in the prior art are of little concern when operating according to the invention.

Figure 4:
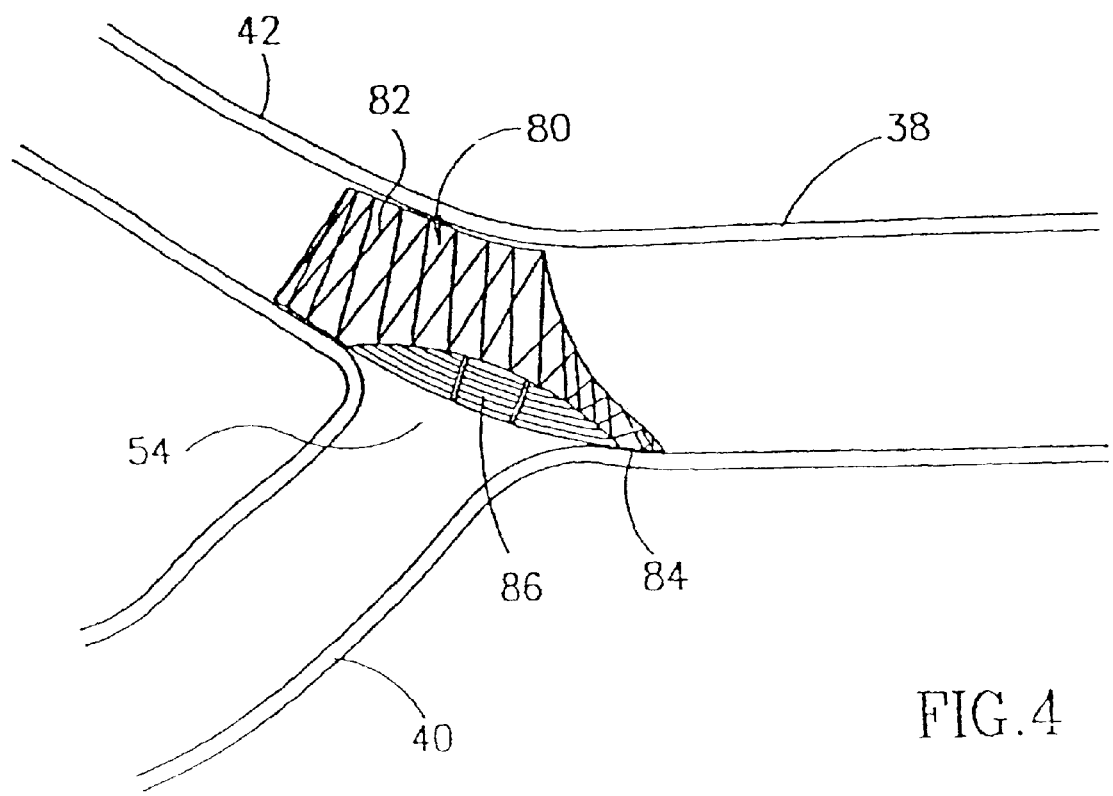
FIG. 4 is a deflecting device wherein the anchoring portion mainly extends into the external carotid artery.

In FIG. 4 there is illustrated another embodiment of a deflecting device, generally designated by numeral 80. This device differs from the embodiments of FIGS. 1 and 2 in that its anchoring portion 82 mainly extends into the external carotid artery 42, with only a minor wall portion 84 thereof extending into the common carotid artery 38. It is noted that the deflecting member 86 is positioned across inlet 54 of the ICA 40.

Figure 5:
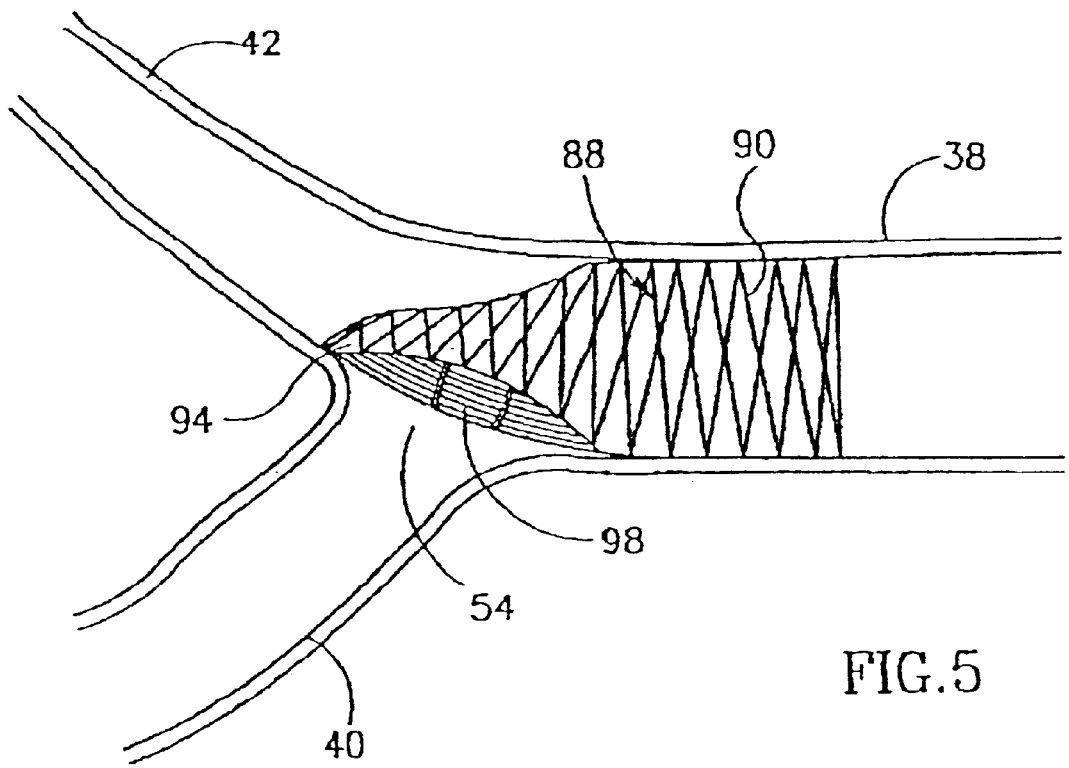
FIG. 5 is a deflecting device in which the anchoring portion extends mainly in the common carotid artery.

Still another embodiment of a deflecting device 88 is illustrated in FIG. 5, which again is similar to the embodiments of FIGS. 1, 2 and 4, the main difference being in the size and shape of the anchoring member 90. Different designs of deflecting members in accordance with the invention may be chosen by physicians for use in a given situation, depending on several physiological parameters of the patient. In the design of FIG. 5, the deflecting member 98 has its anchoring portion 90 extending within the common carotid artery 38, with a minor portion 94 bearing against a wall of the external carotid artery 42. Here again, it is noted that the deflecting member 98 extends across the inlet 54 of ICA 40.

It should be noted that the deflecting member in accordance with each of the embodiments of the invention is so sized and shaped as to facilitate correct positioning across the inlet of the internal carotid artery 40. For that purpose, it is required that the deflecting member be somewhat larger than the cross-sectional size of the inlet into the ICA.

Figure 6:
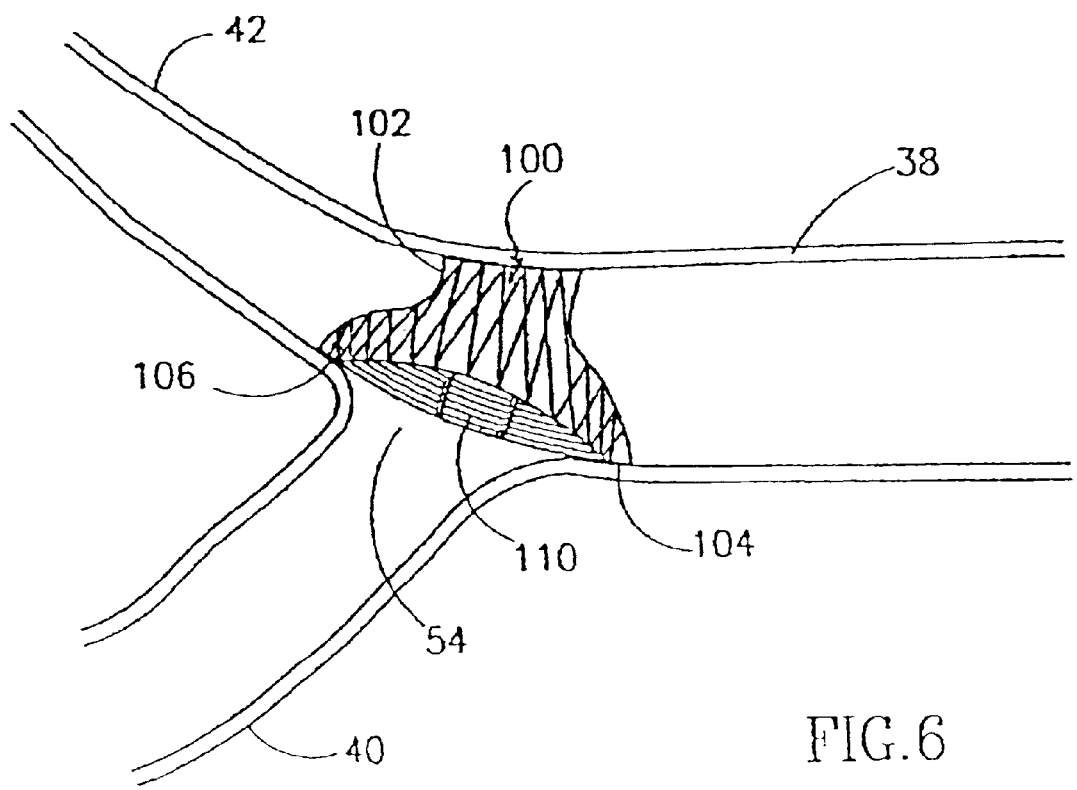
FIG. 6 is a deflecting device in which the anchoring portion is located at the bifurcation zone.

FIG. 6 illustrates still a further embodiment of a deflecting device, according to another preferred embodiment of the invention, generally designated at 100, wherein the anchoring member 102 extends within the zone of bifurcation, with a wall portion 104 bearing against the common carotid artery 38 and a second portion 106 bearing against a wall portion of the external carotid artery 42. Deflecting surface 110 is similar to that of the previous embodiments, and extends across inlet 54 of the internal carotid artery 40.

The device of the invention can be constructed in a way very similar to cardiac stents, although the dimensions are different and, therefore, allow for greater constructive flexibility. However, the man of the art will easily recognize the materials and expandable shapes suitable to make the stent of the invention. For instance, the stent and the deflecting device can be made of a material selected from nitinol, polymeric material stainless steel, etc., and having a configuration selected from zigzag shape and sinusoidal shape. The filtering means of the deflecting device, if used, should have the following dimensions, in order to effectively prevent the entrance of at least a major part of dangerous embolic material: >200–400 $\mu$m. The diameter of the stent may somewhat vary for different individuals. However, the diameter in the closed state is p to about 3 mm, while when expanded, the diameter may vary in the range of 5 mm to 10 mm. The diameter of the wire which makes up the body (or anchoring portion) of the device is preferably in the range 100 $\mu$m to 200 $\mu$m, while that of the wire used for the filtering device is preferably in the range of 10 $\mu$m to 200 $\mu$m. Of course, the entire device can also be constructed using the same dimensions, so that there is no difference in mesh size between the body of the device and its deflecting portion.

The device of the invention must fulfill certain predetermined conditions that will be detailed hereinafter. The skilled person will of course be able to devise various devices, of different shapes and properties, which fulfill said conditions. When testing a device of the invention under physiological conditions, namely:

$Re_{av}$=200–500

BPM (beats per minute)=40–180

Womersley=2–7 wherein $Re_{av}$ is the average Reynolds number, and Womersley is the dimensionless beat parameter;
the following conditions should preferably be met by the device of the invention:

1) $Re_{prox}$ between 0 and 4, preferably 1 or less (creeping or Stokes' flow)
2) 100 dyne/cm$^2$>Shear Stress>2 dyne/cm$^2$
3) The generation of thrombin should not exceed 40 nmole/minute, as measured according to the thrombin acetylation test.

wherein $Re_{prox}$ is the Reynolds number for the wire of which the deflecting element is made, and the shear stress is measured at the device. As will be appreciated by the skilled person, the smaller the $Re_{prox}$ number the better. However, devices attaining larger $Re_{prox}$ numbers than indicated above may also be provided, and the invention is by no means limited to any specific $Re_{prox}$ number.

Figure 8:
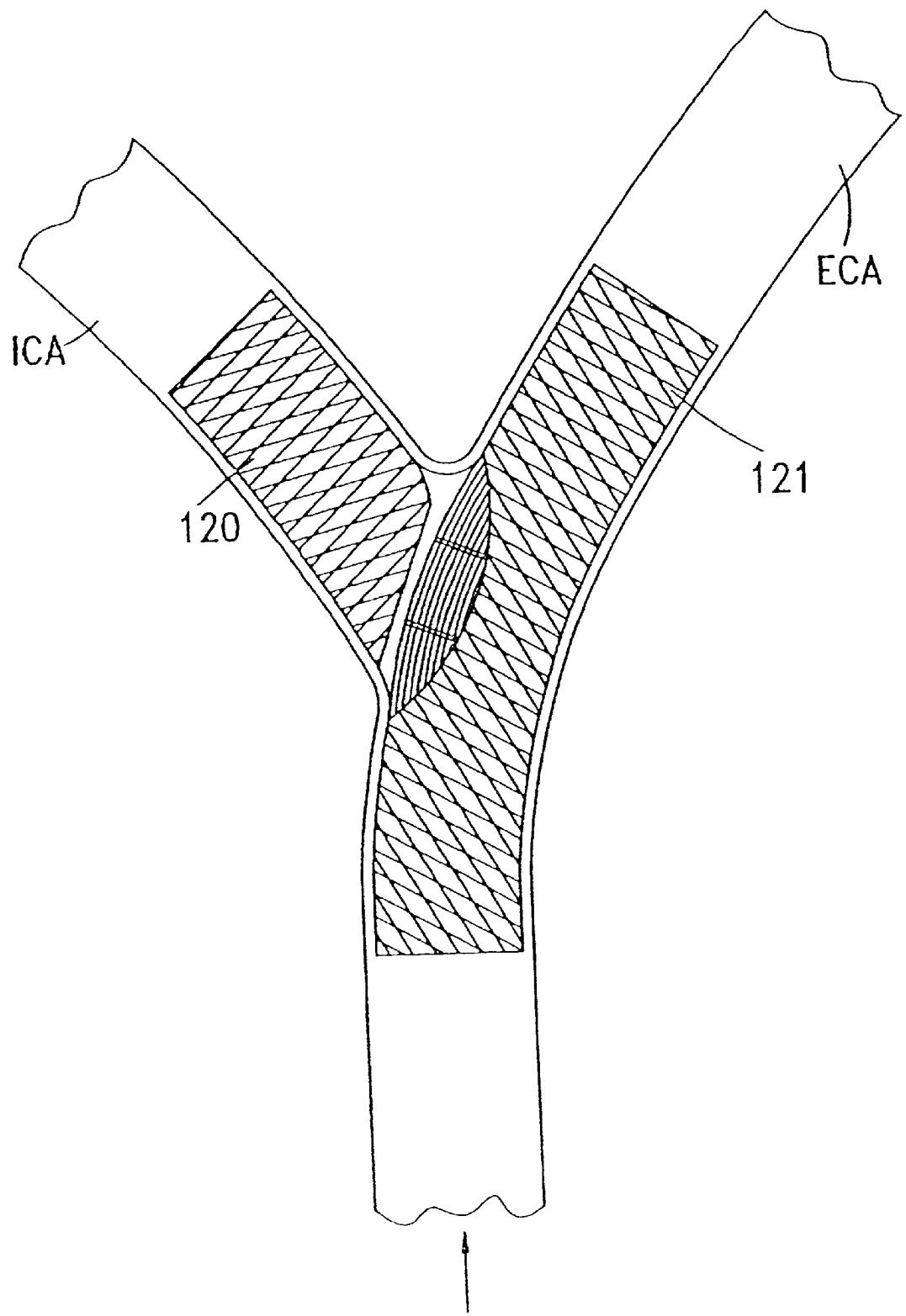
FIG. 8 schematically shows how to deal with a bifurcation lesion, according to one preferred embodiment of the invention.

The device of the invention can be utilized in a variety of ways. A suitable procedure is illustrated in FIG. 8. In the figure, the ICA-ECA bifurcation is shown, after treatment for a bifurcation lesion. The blood flows in the direction of the arrow. This lesion is treated as follows:

1. Firstly, the occlusions are opened using conventional angioplastic techniques;
2. Then, a normal stent 120 is introduced in the ICA,
3. The catheter used to introduce stent 120 is retracted, and the device of the invention, indicated by numeral 121, is then introduced. The resulting situation is seen in the figure.

Of course, the procedure and devices illustrated in FIG. 8 are only one option to treat a bifurcation lesion, and other alternative devices and methods exist, which are well known to the skilled person, and which are not described herein, for the sake of brevity.

The invention is useful in a variety of cases. Some illustrative indications are listed below:

1) Severe carotid stenosis with concomitant high risk proximal sources of emboli. These are, for instance:
   Protruding Aortic arch atheroma (more than ⅓ of symptomatic patients);
   Severe carotid stenosis with concomitant cardiac disease;
   Severe carotid stenosis in patients undergoing heart surgery (5% on the statistical basis of 600,000 coronary bypass surgery)
2) Embolic strokes from proximal sources (e.g., mechanical heart valves, Afib, LVT, protruding AAA). These are:
   Atrial fibrillation (2.5 million in the U.S.A. in 1999);
   Mechanical heart valve (225,000 procedures performed annually in the U.S.A.);
   Patients at high risk for recurrent embolism for a certain period (S.B.E.);
   Patients at high risk for proximal emboli and absolute contraindications for anticoagulation;
   Patients at high risk for proximal emboli failing best medical treatment.

While some preferred embodiments of the invention have been illustrated and described in the specification, it will be understood by a skilled artisan that it is not intended thereby to limit the disclosure of the invention in any way, but rather it is intended to cover all modifications and arrangements falling within the scope and the spirit of the present invention. For example, the deflecting device may be a permanent device or may be removed from the vicinity of the carotid arteries at need. Furthermore, the deflecting member may be integrally formed with, or detachably connected to, the anchoring member, wherein in some instances it might be necessary first to position the anchoring member and then to attach the deflecting member. Additionally, the deflecting member may be of different size, shape and pattern, depending on flow parameters and patient specific requirements.

What is claimed is:

1. A method for preventing the flow of embolic material flowing in the CCA from accessing the ICA, comprising deflecting the flow of said embolic material into the ECA.

2. A method according to claim 1, comprising implanting in the vicinity of the bifurcation of the common carotid artery (CCA) into the internal carotid artery (ICA) and the external carotid artery (ECA), a deflecting device comprising a deflecting element suitable to deflect the flow of embolic material flowing in the CCA toward the ICA, into the ECA.

3. A method for treating a patient suffering from, or suspected of suffering from, the generation of embolic material, comprising deflecting the flow of said embolic material into the ECA.

4. A method according to claim 3, wherein the deflecting device is provided in, or coupled to, a stent.

5. An intravascular device for implanting in a bifurcation of the common carotid artery (CCA) into the internal carotid artery (ICA) and the external carotid artery (ECA), comprising:
   an implantable body configured and dimensioned for implanting in said bifurcation;
   said implantable body including a deflecting portion sufficiently large to span said ICA at the bifurcation and having openings of a size to deflect, from said ICA to said ECA, embolic material in the blood flow from said CCA, while allowing blood flow from said CCA to said ICA;
   wherein said deflecting portion comprises an array of wires extending adjacent said ICA, and wherein the wires have a thickness between 10–50 $\mu$.

6. An implantable device according to claim 5, wherein the Reynolds number for the wire is between 0 and 4, preferably 1 or less.

7. A device according to claim 5, wherein the deflecting portion comprises filtering means.

8. The device according to claim 5, wherein the size of the openings in said deflecting portion is such as to deflect, from said ICA to said ECA, particles in the range of 200 $\mu$m in size.

9. The device according to claim 5, wherein said implantable body is tubular in configuration, and said deflecting portion is an annular section of said tubular body extending for the complete circumference of said tubular implantable body.

10. The device according to claim 5, wherein said implantable body is tubular in configuration, and said deflecting portion is a section of said tubular body at one side, and extending for less than the complete circumference, of said tubular implantable body.

11. The device according to claim 5, wherein said implantable body is tubular in configuration and is configured and dimensioned for implanting within said ICA, and said deflecting portion extends across the end of said ICA at said bifurcation to deflect said embolic material to said ECA.

12. The device according to claim 5, wherein said implantable body is in a radially contracted state when introduced into said bifurcation, and is radially expandable to become anchored in the walls of said bifurcation when implanted therein.

13. The device according to claim 5, wherein said implantable body is configured and dimensioned to span said bifurcation between said CCA and said ECA, with said deflecting portion facing and spanning said ICA at said bifurcation.

14. The device according to claim 5, wherein said body includes radio-opaque markers for aiding in the intravascular positioning of the device.

15. The device according claim 5, wherein said implantable body is configured and dimensioned to have one end thereof positionable in the CCA and another end thereof positionable in the ECA.

16. An intravascular device for implanting in a bifurcation of the common carotid artery (CCA) into the internal carotid artery (ICA) and the external carotid artery (ECA), comprising:
   an implantable body configured and dimensioned for implanting in said bifurcation;
   said implantable body including a deflecting portion sufficiently large to span said ICA at the bifurcation and having openings of a size to deflect, from said ICA to said ECA, embolic material in the blood flow from said CCA, while allowing blood flow from said CCA to said ICA;
   wherein said implantable body is tubular in configuration, and said deflecting portion is a section of said tubular body at one side, and extending for less than the complete circumference, of said tubular implantable body.

17. An intravascular device according to claim 16, wherein said deflecting portion comprises an array of wires extending adjacent said ICA, and wherein the wires have a thickness between 10–150μ.

18. An implantable device according to claim 16, wherein the Reynolds number for the wire is between 0 and 4, preferably 1 or less.

19. The device according to claim 16, wherein the size of the openings in said deflecting portion is such as to deflect, from said ICA to said ECA, particles in the range of at least 200 μm in size.

20. The device according to claim 16, wherein said implantable body is tubular in configuration and is configured and dimensioned for implanting within said ICA, and said deflecting portion extends across the end of said ICA at said bifurcation to deflect said embolic material to said ECA.

21. The device according to claim 16, wherein said implantable body is in a radially contracted state when introduced into said bifurcation, and is radially expandable to become anchored in the walls of said bifurcation when implanted therein.

22. The device according to claim 16, wherein said implantable body is configured and dimensioned to span said bifurcation between said CCA and said ECA, with said deflecting portion facing and spanning said ICA at said bifurcation.

23. The device according to claim 16, wherein said body includes radio-opaque markers for aiding in the intravascular positioning of the device.

24. The device according claim 16, wherein said implantable body is configured and dimensioned to have one end thereof positionable in the CCA and another end thereof positionable in the ECA.

* * * * *